(12) United States Patent
de Haan et al.

(10) Patent No.: US 11,013,484 B2
(45) Date of Patent: May 25, 2021

(54) DOSE SENSING PIXELS REFERENCE VOLTAGE

(71) Applicant: Teledyne DALSA B.V., Thousand Oaks, CA (US)

(72) Inventors: Willem Johan de Haan, Eindhoven (NL); Daniel Wilhelmus Elisabeth Verbugt, Helden (NL)

(73) Assignee: TELEDYNE DALSA B.V., Thousand Oaks, CA (US)

( * ) Notice: Subject to any disclaimer, the term of this patent is extended or adjusted under 35 U.S.C. 154(b) by 38 days.

(21) Appl. No.: 16/370,778

(22) Filed: Mar. 29, 2019

(65) Prior Publication Data

US 2019/0298293 A1    Oct. 3, 2019

(30) Foreign Application Priority Data

Mar. 29, 2018  (EP) ..................... 18165189

(51) Int. Cl.
| | |
|---|---|
| *A61B 6/00* | (2006.01) |
| *G01T 1/20* | (2006.01) |
| *H04N 5/32* | (2006.01) |
| *H04N 5/345* | (2011.01) |
| *H04N 5/374* | (2011.01) |
| *H04N 5/361* | (2011.01) |
| *H04N 5/378* | (2011.01) |
| *H04N 5/343* | (2011.01) |

(52) U.S. Cl.
CPC ............ *A61B 6/542* (2013.01); *A61B 6/4233* (2013.01); *G01T 1/2018* (2013.01); *H04N 5/32* (2013.01); *H04N 5/343* (2013.01); *H04N 5/345* (2013.01); *H04N 5/361* (2013.01); *H04N 5/374* (2013.01); *H04N 5/378* (2013.01)

(58) Field of Classification Search
None
See application file for complete search history.

(56) References Cited

U.S. PATENT DOCUMENTS

| | | | | |
|---|---|---|---|---|
| 7,352,840 | B1 * | 4/2008 | Nagarkar | A61B 6/032 250/363.02 |
| 8,076,647 | B2 * | 12/2011 | Danielsson | G01T 1/00 250/370.11 |
| 2012/0002083 | A1 | 1/2012 | Machida | |
| 2015/0163424 | A1 | 6/2015 | Morino et al. | |
| 2019/0379853 | A1 * | 12/2019 | Kawazu | H04N 5/37455 |

FOREIGN PATENT DOCUMENTS

EP  0926885  6/1999

OTHER PUBLICATIONS

European Search Report for EP18165189.4, dated Jan. 16, 2019.

* cited by examiner

*Primary Examiner* — Edwin C Gunberg
(74) *Attorney, Agent, or Firm* — Snell & Wilmer LLP

(57) ABSTRACT

The present invention relates to an image sensor and to an X-ray system comprising such image sensor. More in particular, the invention relates to an image sensor wherein dose sensing pixels are used in conjunction with artificial pixels to sense a dose of incoming light or radiation.

According to the invention, the image sensor comprises one or more shielded photo-sensitive pixels that are shielded for incoming photons and which are each configured for outputting a further reference voltage, wherein the input voltage of the artificial pixels is set in dependence on the outputted further reference voltage(s).

15 Claims, 8 Drawing Sheets

DOSE SENSING PIXELS REFERENCE VOLTAGE

CROSS-REFERENCE TO RELATED APPLICATIONS

The present application is a U.S. national phase entry of and claims priority from European Application No. EP 18165189.4, filed on Mar. 29, 2018, which is hereby fully incorporated herein by reference in its entirety.

The present invention relates to an image sensor and to an X-ray system comprising such image sensor. The invention further relates to an optical recording system, such as an optical camera, comprising the image sensor.

In X-ray systems used for medical imaging, it is important that the patient is not subjected to excessive X-ray radiation. On the other hand, a sufficient dose of X-rays is required to properly image a region of interest, such as a lesion. Hence, when subjecting a patient to X-rays, the amount of X-rays that is not used for medical imaging should be minimized. This is particularly relevant for X-ray systems in which the X-ray source is not synchronized with the X-ray image sensor. Hereinafter, such system will be referred to as a non-synchronized system.

In non-synchronized X-ray systems, the X-ray image sensor may be equipped with one or more dose sensing pixels. An example of such a sensor is illustrated in FIG. 1. The known X-ray image sensor 1 comprises a matrix 2 of rows and columns of photo-sensitive pixels 3. Some of these pixels are designated as dose sensing pixels 4.

X-ray image sensor 1 is operable in a dose sensing mode, in which a dose of incoming photons is sensed using the one or more dose sensing pixels, and an image read-out mode, in which image information is determined using the matrix of pixels based on a received dose of incoming photons. Typically, in the image read-out mode, each pixel in the matrix is used, including the dose sensing pixels, whereas in the dose sensing mode only the dose sensing pixels are used. However, the invention equally relates to embodiments wherein the dose sensing pixels are only used in the dose sensing mode.

To enable read-out of the pixels, X-ray image sensor 1 comprises a pixel controller 5 that includes selecting circuitry 5' for selecting one or more rows of pixels in the matrix. X-ray image sensor 1 further comprises read-out circuitry 6 configured for reading out the selected pixels. Due to the matrix configuration, only one pixel can be selected for each column as pixels on the same column share a single column line 7 for feeding the voltages to read-out circuitry 6. By arranging the dose sensing pixels in the manner illustrated in FIG. 1, it becomes possible to select all the dose sensing pixels at the same time although they are distributed over different rows because only a single (or none) dose sensing pixel will be selected for each column.

FIG. 2 illustrates a known layout for a pixel. This layout is known as a 3T layout as it comprises three transistors. The pixel comprises a (pinned) photodiode 10, a primary storage capacitor 11, and a secondary storage capacitor 12 which can be switched using a switch 13. Typically, a scintillator layer (not illustrated) is applied over the pixel or is integrated therewith. This layer converts incoming X-rays into visible light which can be detected by photodiode 10. The operation of the pixel can be explained as follows. As a first step, the voltage at the terminal between capacitor 11 and photodiode 10 is charged/reset to a predefined reference voltage (Vref) using a NMOST 14 in response to a reset signal (reset0) received from pixel controller 5. Next, NMOST 14 is brought into a non-conducting state. When light falls onto photodiode 10, it generates charges which are transferred to capacitor 11. Consequently, the voltage at the terminal of capacitor 11 will decrease depending on the incident light. After a predetermined time, e.g. the integration time, the voltage at this terminal is sensed using a source follower NMOST 15 that is connected to a supply voltage Vsupply and to an NMOST 16 that acts as a selection FET. More in particular, in response to a select signal (select0) from selecting circuitry 5', the voltage at the terminal of capacitor 11, referred to as the photo-voltage (Vphoto), is fed through source follower 15 and selection FET 16 to read-out circuitry 6 via output terminal (out0), which terminal is connected to pixel column line 7. There, the analog signal is converted into a digital value, e.g. using an analog-to-digital converter. As a final step, selection FET 16 is brought into a non-conductive state and the process is repeated.

By closing switch 13 in response to receiving a capacitance select signal (capselect) from pixel controller 5, secondary storage capacitor 12 can be put parallel to primary storage capacitor 11. This allows the pixel to process a higher dose of X-rays as the effective storage capacitance has increased, and to thereby offer a different sensitivity. The skilled person will understand that having a secondary storage capacitor is optional. Hereinafter, second capacitor 12 and switch 13 will therefore be disregarded. It should also be noted that the invention equally relates to embodiments wherein storage capacitor 11 is intrinsically present in photodiode 10.

The fabrication of the pixel is subjected to process variation. For example, the voltage that is read out does not exactly correspond to the photo-voltage over first storage capacitor 11. More in particular, the voltage drop over source follower 15 may cause an undesired variation in the read out voltage. In other words, although the voltage over first capacitor 11 may be identical for different pixels, the actual voltage that is read out may differ.

To solve this problem, it is known to use a double data sampling (DDS) technique. This technique uses a separate resetting step in which the voltage over first storage capacitor 11 is read out directly after resetting this voltage. During the integration time, the photo-voltage over the first storage capacitor will decrease to a value equal to Vphoto=Vref−Vint, wherein Vint is the voltage decrease due to charge accumulation during the integration time in first storage capacitor 11. Reading out Vphoto by read-out circuitry 6 will introduce an offset (Voff), which offset is subject to process variations. Referring to the read out voltage as V1, one finds that V1=Vphoto−Voff=Vref−Vint−Voff.

When reading out the voltage directly after the resetting step described above, Vint will be zero. Hence, referring to the read out voltage as V2, one finds that V2=Vref−Voff. The pixel voltage for a given pixel (Vpixel) can then be determined using Vpixel=V2−V1=Vint. Hence, by using the DDS technique it becomes possible to mitigate the influence of process variations on the voltages that are read out. However, this technique requires a reset.

Now referring to FIG. 3, the concept of using dose sensing pixels will be explained. Here, a non-synchronized system is used wherein the X-ray source will at a given moment in time (t0) start to emit X-rays, as illustrated in the top graph in FIG. 3. This moment in time is unknown to the X-ray image sensor. To this end, X-ray image sensor will operate in the dose sensing mode. In this mode, the dose sensing pixels are repeatedly read out and the resulting voltage is compared to a threshold. If this threshold is exceeded, it is determined that the X-ray source has started to emit X-rays and the operating mode of the X-ray image sensor will change to the image read-out mode.

To compare the pixel voltages to the threshold, a respective threshold may be used for each column in which a dose sensing pixel is arranged. Then, if the respective thresholds are exceeded for a predetermined amount of pixels, the operating mode may switch to the image read-out mode. Alternatively, an average pixel voltage may be determined for the dose sensing pixels, which voltage is compared to a threshold. It should be apparent that alternative methods are possible.

In FIG. 3, line 30 displays the pixel voltage versus time for an ideal X-ray image sensor. During the time interval between t0 and t1 the pixel voltage will increase as a result of the sensed dose of X-rays. Prior to t=t0, the pixel voltage will remain zero as no X-rays are detected. After t=t1, the threshold indicated by line 31 will be exceeded and the X-ray image sensor will switch to the image read-out mode. Depending on the threshold, there will be more or less loss in X-rays, indicated by area 32. This area represents the dose of X-rays that is not used for the actual capturing of the X-ray image. This area should be minimized.

To accurately determine the pixel voltage, a DDS technique should be used. However, as stated above, this would require a reset of the dose sensing pixels. It may happen that the reset is performed at a time where the X-ray has just started to emit X-rays. In this, a relatively large loss of X-rays will occur. In addition, the process of resetting may be time-consuming.

To solve this problem, the known image sensor comprises one or more artificial pixels 8 for providing a reference voltage, see FIG. 1. These artificial pixels typically comprise those components of the 3T pixel layout that would introduce process or manufacturing related offsets in the pixel voltage. For example, artificial pixels 8 may comprise a source follower and a select transistor.

FIG. 4 illustrates an example of an artificial pixel 8. An artificial pixel is typically provided for each column and is arranged at the lower or upper side of the matrix. The artificial pixel comprises, in addition to source follower 815, a select transistor 816. These transistors are connected in a manner similar to the corresponding transistors 15, 16 of the pixel in FIG. 2. In other words, the output (out1) of artificial pixel 8 is connected to column line 7. A select signal (select1) from select circuitry 5' is used for selecting the artificial pixel. The input voltage (Vin) used is identical to the reference voltage (Vref) used for the other pixels.

The objective of the artificial pixels is to output a reference voltage that matches the voltage outputted by the dose sensing pixels directly after reset as closely as possible. This outputted reference voltage is then used as V2 in the DDS technique to compute a pixel voltage for the dose sensing pixels. In the known X-ray image sensor, the outputted reference voltage by the artificial pixels equals Vref−Voff.

Actual X-ray image sensors will suffer from what is known as dark current. This current will flow even in the absence of X-rays. This parasitic current will change the voltage over first storage capacitor 11. Line 33 in FIG. 3 illustrates the detected pixel voltage of the dose sensing pixels taken into account dark current. As can be seen, line 33 could eventually cross threshold line 31 even before the X-ray source has commenced emitting X-rays. This would inadvertently trigger a switch to the image read-out mode.

To prevent the inadvertent switching to the image read-out mode, the dose sensing pixels in the known X-ray image sensors have to be occasionally reset, again introducing the risk of excessive X-ray dose loss. By increasing the threshold the amount of times that the dose sensing pixels have to be reset can be lowered. Then again, an increased threshold would result in a higher loss of X-rays as area 32 would increase.

The Applicant has found that it is difficult to meet the increasingly more stringent requirements with respect to the maximum dose of lost X-rays that can be tolerated using the known X-ray image sensors.

It is therefore an object of the present invention to provide an X-ray image sensor in which these requirements can be met or can be met more easily.

To this end, the present invention provides an X-ray image sensor that is characterized in that it comprises one or more shielded photo-sensitive pixels that are shielded for incoming photons and which are each configured for outputting a further reference voltage, wherein the input voltage of the one or more artificial pixels is set in dependence on the outputted further reference voltage(s).

According to the invention, the voltage outputted by the artificial pixels now reflects the impact of the dark current contrary to prior art approaches in which the artificial pixels do not comprise photo-sensitive elements and in which dark currents do not or hardly occur.

As an example, the voltage read out from a dose sensing pixel may equal V1=Vref−Vint−Voff−Vdark, wherein Vdark is the voltage decrease due to dark current. Furthermore, the voltage (V3) outputted by the shielded photo-sensitive pixel may equal V3=Vref−Vdark. Using this voltage as the input voltage (Vin) for the artificial pixel results in the voltage read out from this pixel equaling V2=Vref−Vdark−Voff. Subtracting V1 from V2 results in Vpixel=Vint.

A plurality of the one or more shielded photo-sensitive pixels may be grouped. The image sensor may further comprise a determining unit for determining a voltage to be set as the input voltage for at least some of the artificial pixels based on the further reference voltages outputted by the group of shielded photo-sensitive pixels. The dark current in a pixel strongly depends on the amount and nature of surface states in that pixel. Typically, there exists a strong variation in dark currents over the semiconductor wafer even between adjacent pixels or pixel regions. It may therefore be advantageous to base the determination of the input voltage to be used by the artificial pixels not only on a single shielded photo-sensitive pixel. By grouping these pixels together and by determining the input voltage based on the further reference voltages outputted by these pixels, the impact of the variation of dark current can be mitigated. Different groups of shielded photo-sensitive pixels may be used for different groups of artificial pixels. Furthermore, a group of shielded photo-sensitive pixels and the group of artificial pixels for which it supplies the input voltage may be arranged close to each other.

As an example, the determining unit may be configured for determining the voltage to be set as the supply voltage for the at least some of the artificial pixels on the basis of a maximum voltage, an average voltage, or a median voltage among the outputted further reference voltages, or on the basis of an average or median voltage among the outputted further reference voltages determined while disregarding one or more of the lowest and/or highest voltages. By disregarding the lowest or highest voltages, the impact on the pixel voltage for a given dose sensing pixel of a shielded photo-sensitive pixel with abnormal dark current behavior can be mitigated. If the shielded photo-sensitive pixel excessively suffers from dark current, it will output a relatively low voltage, i.e. V3=Vref−Vdark1, with Vdark1 being the voltage decrease in the shielded photo-sensitive pixel due to dark current. This will result in the pixel voltage for a dose sensing pixel to become Vpixel=V2−V I=(Vref−Vdark1−Voff)−(Vref−Vdark0−Vint−Voff)=Vint−(Vdark1−Vdark0), with Vdark0 being the voltage decrease in dose sensing pixel due to dark current. Hence, if Vdark1>Vdark0, it will take longer for the pixel voltage to exceed the threshold, thereby resulting in a larger dose loss. It may therefore be advantageous to attribute more weight to the relatively high outputted reference voltages.

The image sensor may comprise a buffer for buffering the further reference voltage and/or for buffering the voltage determined by the determining unit, and for supplying the buffered further reference voltage or the buffered determined voltage to at least some of the artificial pixels as the input voltage. The buffer is configured to prevent a capacitive or resistive loading of the shielded photo-sensitive pixel such that the process of obtaining the further reference voltage does not influence the generation of this voltage.

Typically, the shielded photo-sensitive pixels may be arranged outside of the matrix to prevent black spots in the final image. The shielded photo-sensitive pixels may comprise a metal shielding arranged over at least the photo-sensitive part(s) of the shielded photo-sensitive pixel, such as a photodiode. Additionally or alternatively, the photo-sensitive part(s) is/are covered by an opaque layer.

Each of the photo-sensitive pixels and the shielded photo-sensitive pixels may comprise a photodiode having a first terminal and a second grounded terminal, a storage capacitor electrically connected to the photodiode and having a first terminal connected to the first terminal of the photodiode and a second grounded terminal, and a reset unit configured for setting a voltage at the first terminal of the storage capacitor equal to a predefined voltage in dependence of a reset signal received from the pixel controller. Furthermore, at least the photo-sensitive pixels among the photo-sensitive pixels and the shielded photo-sensitive pixels may each further comprise a select unit for allowing the pixel to be selected in dependence of a select signal received from the selecting circuitry, and a forward unit for forwarding the voltage at the first terminal of the storage capacitor to an output of the pixel, when this pixel is selected by the selecting circuitry. It may equally be possible that the shielded photo-sensitive pixels also comprise a forward unit and a select unit. However, it is preferred that these units are configured such that the voltage at the first terminal is substantially continuously outputted. The select unit and reset unit may each comprise a metal-oxide-semiconductor field-effect transistor (MOSFET) and wherein the forward unit comprises a MOSFET source follower. In an embodiment, each of the photo-sensitive pixels and the shielded photo-sensitive pixels may have a 3T layout.

The artificial pixel may comprise a select unit and a forward unit as described above, wherein the artificial pixel is configured to forward, using the forward unit, the input voltage to an output of the artificial pixel, when this pixel is selected by the selecting circuitry.

An artificial pixel may be provided for each column of the matrix of photo-sensitive pixels. Furthermore, the photo-sensitive pixels and artificial pixels that are associated with the same column of the matrix may have their outputs coupled to the same column line.

In the image read-out mode, the selecting circuitry and read-out circuitry may be configured for sequentially selecting a row of pixels of the matrix, the row including the dose sensing pixel(s) in that row, if any, and for determining a pixel voltage for each of the selected pixels. Determining the pixel voltage for each of the selected pixels may comprise the steps of: resetting the photo-sensitive pixels in a row of interest, allowing the reset pixels to capture incoming photons during an integration time, after expiry of the integration time, reading out voltages associated with the pixels in the row of interest as first voltages, resetting the pixels in the row of interest and directly thereafter reading out voltages associated with these pixels as a second voltage, and determining pixel voltages for the pixels in the row of interest by subtracting the first voltages from the second voltages.

In the dose sensing mode, the selecting circuitry may be configured for simultaneously selecting dose sensing pixels that are arranged in different rows. Furthermore, the read-out circuitry may be configured for determining a pixel voltage for each of the selected dose sensing pixels. Determining the pixel voltage for each of the selected dose sensing pixels may comprise the steps of: resetting the dose sensing pixels, allowing the dose sensing pixels to capture incoming photons, selecting the dose sensing pixels, reading out voltages associated with the selected dose sensing pixels as a first voltage, de-selecting the dose sensing pixels and selecting artificial pixels that are associated with the dose sensing pixels, reading out voltages associated with the selected artificial pixels as a second voltage, determining the pixel voltages for the dose sensing pixels by subtracting the first voltages from the second voltages.

The skilled person readily understands that the present invention is not limited to X-ray sensors but may equally apply to image sensors for optical systems, e.g. image sensors for capturing visible light, ultraviolet light, or infra-red light. However, to enable an image sensor to be used in an X-ray system, at least the matrix of photosensitive pixels is covered with a scintillator layer for converting incoming X-ray photons into visible light photons.

According to a second aspect, the present invention provides an X-ray source for emitting X-ray radiation, and an X-ray detector for detecting the emitted X-ray radiation, wherein the X-ray detector comprises the image sensor with scintillator layer as described above.

According to a third aspect, the present invention provides an optical recording system, such as an optical camera, comprising the image sensor as defined above.

Next, the invention will be described in more detail referring to the appended drawings, wherein.

Figure 5:
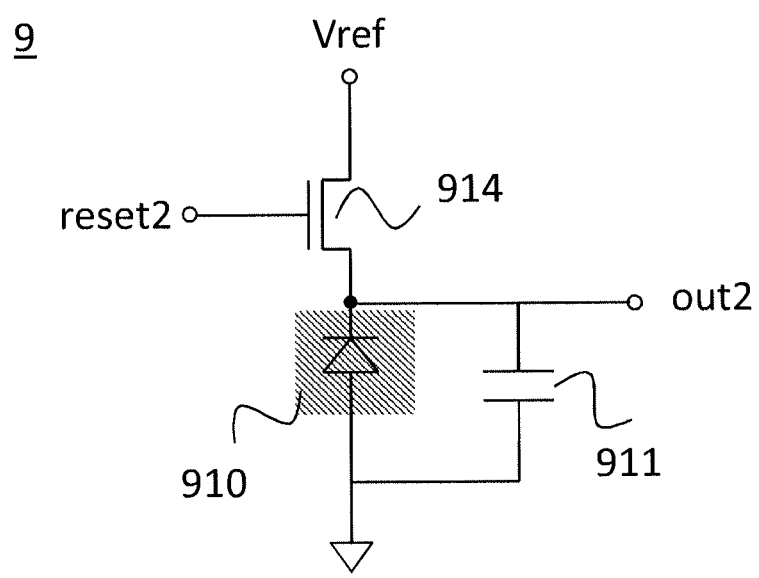
FIG. 5 illustrates an embodiment of a shielded photo-sensitive pixel in accordance with the present invention.

FIG. 5 illustrates an embodiment of a shielded photo-sensitive pixel 9 in accordance with the present invention. It comprises a shielded photodiode 910, a first storage capacitor 911, and a reset transistor 914. If additional storage capacitors are used in the photosensitive pixels in the matrix, they should preferably also be used in the shielded photo-sensitive pixels.

Directly after resetting shielded photo-sensitive pixel 9 using reset transistor 914 in response to a reset signal (reset2) from pixel controller 5, the outputted voltage at terminal out2, V3, will equal Vref, wherein the reference voltage preferably equals the reference voltage used for dose sensing pixels 4 and the other photo-sensitive pixels 3 in the matrix. Thereafter, the voltage at the output will decrease as a result of dark current, i.e. V3=Vref−Vdark.

Figure 1:
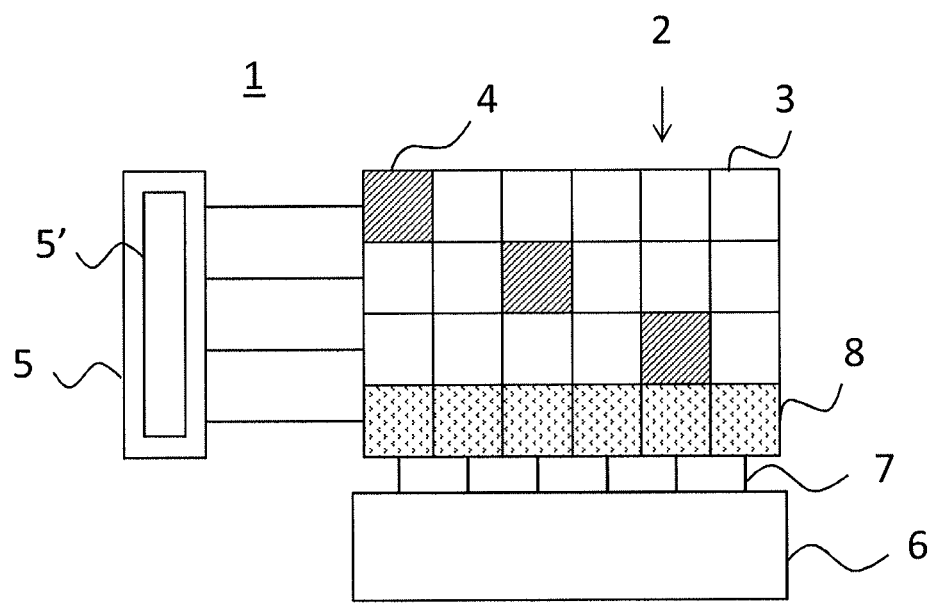
FIG. 1 illustrates an embodiment of a known image sensor.
Figure 2:
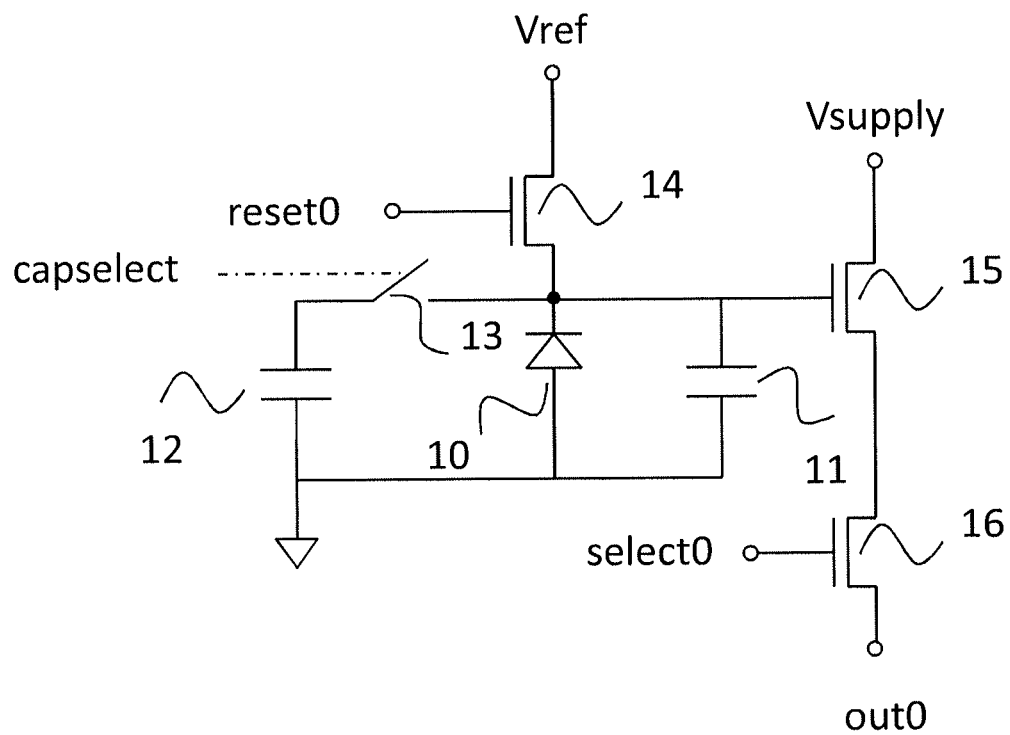
FIG. 2 illustrates a known 3T layout for a pixel.
Figure 4:
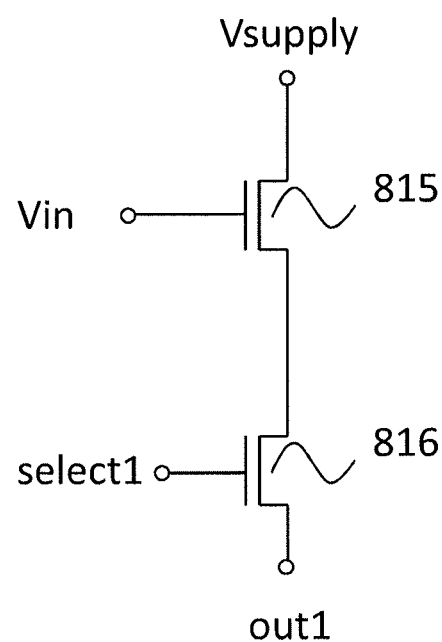
FIG. 4 illustrates an artificial pixel used in the image sensor of FIG. 1.
Figure 6:
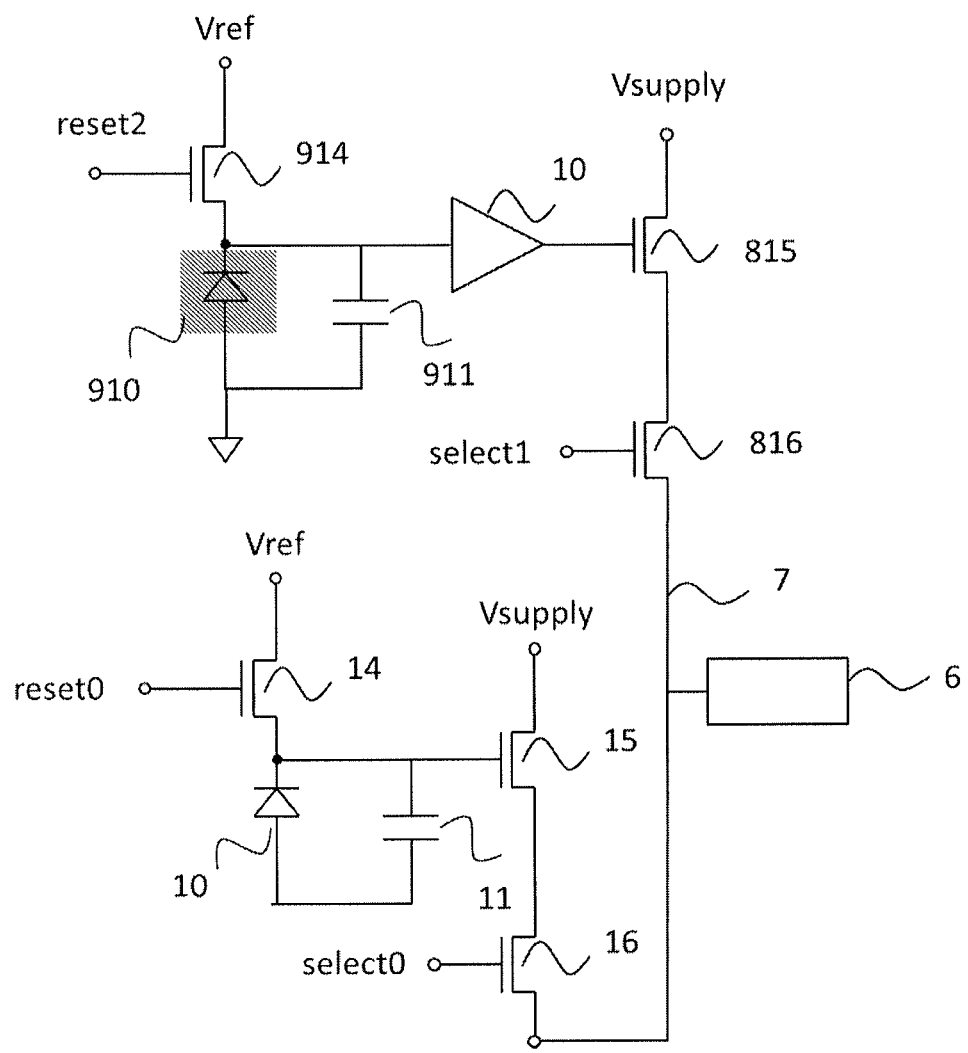
FIG. 6 illustrates part of an embodiment of an image sensor in accordance with the present invention.

FIG. 6 illustrates an embodiment of an X-ray image sensor according to the present invention. The sensor comprises a plurality of dose sensing pixels 4 having a layout as illustrated in FIG. 2, and of which one is shown in FIG. 6. The X-ray image sensor further comprises, for each column, an artificial pixel 8 having a layout as illustrated in FIG. 4 and which is arranged at the lower end of the column. The output of artificial pixel 8 is connected to a respective column line 7. The image sensor further comprises one or more shielded photo-sensitive pixels 9, such as the pixel shown in FIG. 5. The output of this pixel is connected via a buffer 10 to the input of artificial pixel 8.

Figure 3:
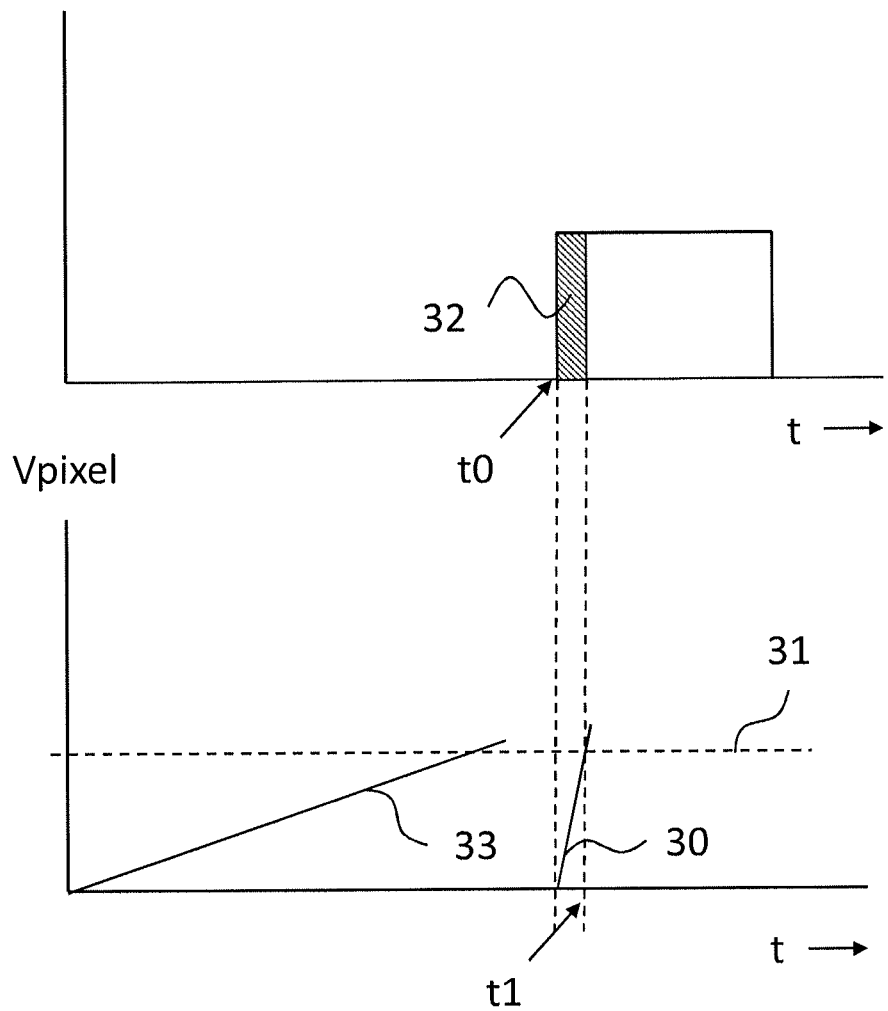
FIG. 3 illustrates the behavior of the known image sensor of FIG. 1.

In the dose sensing mode, read-out circuitry 6 repeatedly reads out the voltages of dose sensing pixels 4 and artificial pixels 8 as described in conjunction with FIG. 3. However, because the output of shielded photo-sensitive pixel 9 is used as the input voltage for artificial pixel 8, the output of the artificial pixel will equal V2=Vin−Voff=Vref−Vdark−Voff. Combined with the output of the dose sensing pixel, i.e. V1=Vref−Vdark−Vint−Voff, the resulting pixel voltage, Vpixel, equals V2−V1=Vint.

In the dose sensing mode, the outputted voltage of the shielded photo-sensitive pixel should not become too small as the resulting voltage headroom would no longer allow the pixel voltage to exceed the threshold. Therefore, the shielded photo-sensitive pixels and the dose sensing pixels should be occasionally reset. However, compared to the known X-ray image sensor discussed in conjunction with FIG. 3, a lower threshold can be used and/or the frequency of resetting the dose sensing pixels can be lowered, thereby resulting in a lower dose loss.

Figure 7:
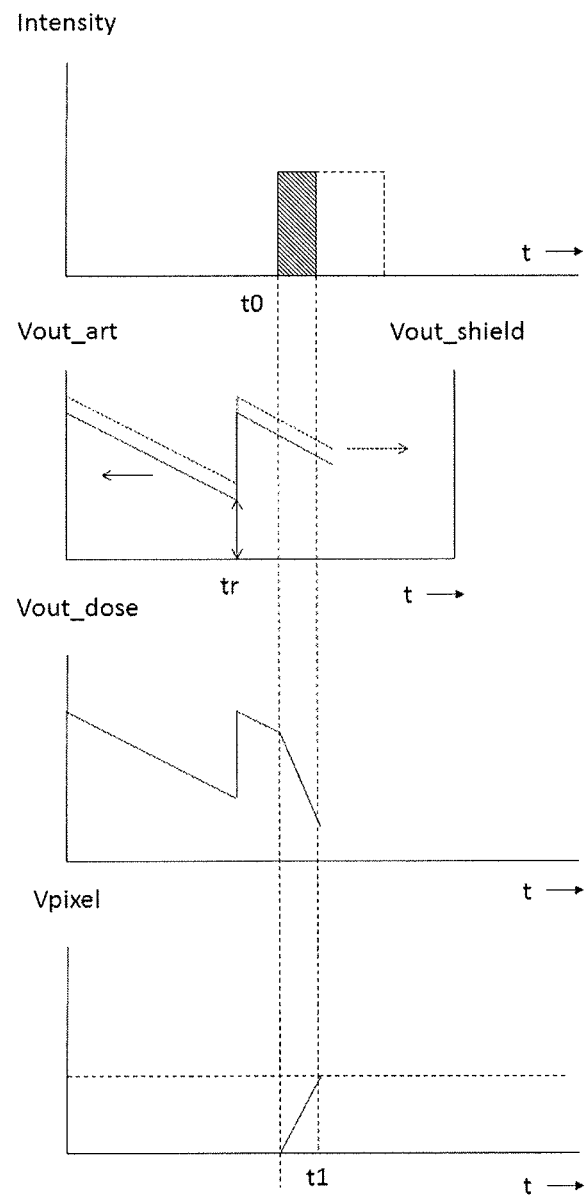
FIG. 7 illustrates the behavior of the image sensor of FIG. 6.

The behavior of the image sensor of FIG. 6 is illustrated in FIG. 7. Here, it can observed that the output of the shielded photo-sensitive pixel Vout_shield=Vin=Vref−Vdark is slightly higher than the output of the artificial pixel Vout_art=V2=Vin−Voff=Vref−Vdark−Voff. The pixel voltage Vpixel can be determined by subtracting the output of the dose sensing pixel Vout_dose=V1=Vref−Voff−Vdark−Vint from Vout_shield, giving Vpixel=Vint. Here, Vint corresponds to the voltage decrease as a result of capturing X-rays emitted by the X-ray source. As can be seen in FIG. 7, the impact of dark currents on the pixel voltage is mitigated.

FIG. 7 illustrates that at t=tr the voltage outputted by the artificial pixel has reached a level that no longer allows the pixel voltage to exceed the threshold. Hence, at t=tr the voltage of the dose sensing pixel and the shielded photo-sensitive pixel are reset.

Figure 8:
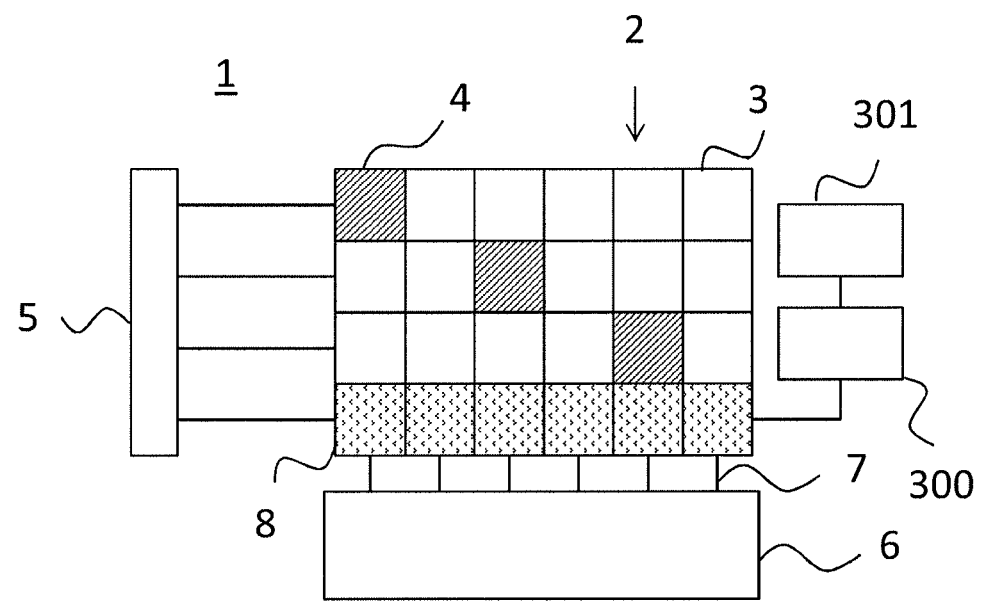
FIG. 8 illustrates a further embodiment of an image sensor in accordance with the present invention.

In FIG. 7, it is assumed that the voltage outputted by the shielded photo-sensitive pixels accurately reflects the impact of dark currents on the voltage outputted by the dose sensing pixels. However, the total amount of dark current depends, inter alia, on the density of surface states. As such, there exists a relatively large variation between the outputted voltages of the various shielded photo-sensitive pixels. If the outputted voltage is indicative of a relatively low dark current, there still may exist an influence of dark current on the pixel voltage associated with the dose sensing pixel as the dark current in the dose sensing pixel may deviate from that in the shielded photo-sensitive pixel. To solve this problem, the invention proposes, in an embodiment, to group a plurality of shielded photo-sensitive pixels into a group 300, see FIG. 8. The outputs of these pixels may be processed by a processing unit 301, which will, based on the outputs of the shielded photo-sensitive pixels, generate a voltage to be used as input voltage by artificial pixels 8. For example, processing unit 301 may be configured to average the outputs of the shielded photo-sensitive pixels, to discard the lowest and/or highest value(s) and to then determine an average, or to select the lowest voltage among the collected voltages from the shielded photo-sensitive pixels, and to use the processed voltage as the input voltage to be used by the artificial pixels.

In the description above, the invention has been explained using detailed embodiments thereof. However, the skilled person will readily understand that invention is not limited to these embodiments but that various modifications can be made without deviating from the scope of the invention, which is defined by the appended claims.

The invention claimed is:

1. An image sensor, comprising:
   a plurality of photo-sensitive pixels arranged in a matrix of rows and columns, said plurality of photo-sensitive pixels having one or more dose sensing pixels, wherein the image sensor is operable in:
   a dose sensing mode, in which a dose of incoming photons is sensed using the one or more dose sensing pixels, and
   an image read-out mode, in which image information is determined using the matrix of pixels based on a received dose of incoming photons;
   one or more artificial pixels for providing a reference voltage in dependence of an input voltage;
   a pixel controller comprising selecting circuitry for selecting one or more rows of pixels in the matrix; and
   read-out circuitry configured for, in the dose sensing mode, reading out respective voltages of selected one or more dose sensing pixels and for determining a respective pixel voltage for each of the selected dose sensing pixels in dependence of the reference voltage and the voltage that was read out for that dose sensing pixel;
   wherein the image sensor further comprises one or more shielded photo-sensitive pixels that are shielded for incoming photons and which are each configured for outputting a further reference voltage, wherein the input voltage of the one or more artificial pixels is set in dependence on the outputted further reference voltage.

2. The image sensor according to claim 1, wherein a plurality of said one or more shielded photo-sensitive pixels are grouped, the image sensor further comprising a determining unit for determining a voltage to be set as the input voltage for at least some of the artificial pixels based on the further reference voltages outputted by the group of shielded photo-sensitive pixels.

3. The image sensor according to claim 2, wherein the determining unit is configured for determining the voltage to be set as the input voltage for said at least some of the artificial pixels on the basis of a maximum voltage, an average voltage, or a median voltage among the outputted further reference voltages, or on the basis of an average or median voltage among the outputted further reference voltages determined while disregarding one or more of the lowest and/or highest voltages.

4. The image sensor according to claim 3, further comprising a buffer for buffering the further reference voltage or for buffering the voltage determined by the determining unit, and for supplying the buffered further reference voltage or the buffered determined voltage to at least some of the artificial pixels as the input voltage.

5. The image sensor according to claim 1, wherein the one or more shielded photo-sensitive pixels are arranged outside of the matrix.

6. The image sensor according to claim 1, wherein the one or more shielded photo-sensitive pixels comprise a metal shielding arranged over at least the photo-sensitive part of the shielded photo-sensitive pixel, or wherein the photo-sensitive part is covered by an opaque layer.

7. The image sensor according to claim 1, wherein each of the photo-sensitive pixels and the shielded photo-sensitive pixels comprise:
   a photodiode having a first terminal and a second grounded terminal;
   a storage capacitor electrically connected to the photodiode and having a first terminal connected to the first terminal of the photodiode and a second grounded terminal; and
   a reset unit configured for setting a voltage at the first terminal of the storage capacitor equal to a predefined voltage in dependence of a reset signal received from the pixel controller.

8. The image sensor according to claim 7, wherein at least the photo-sensitive pixels among the photo-sensitive pixels and the shielded photo-sensitive pixels each further comprise:
   a select unit for allowing the pixel to be selected in dependence of a select signal received from the selecting circuitry; and
   a forward unit for forwarding the voltage at the first terminal of the storage capacitor to an output of the pixel, when the pixel is selected by the selecting circuitry;
   wherein the select unit and reset unit preferably each comprise a metal-oxide-semiconductor field-effect transistor (MOSFET) and wherein the forward unit comprises a MOSFET source follower.

9. The image sensor according to claim 1, wherein the artificial pixel comprises a select unit and a forward unit as the select unit, wherein the artificial pixel is configured to forward, using the forward unit, the input voltage to an output of the artificial pixel, when the pixel is selected by the selecting circuitry.

10. The image sensor according to claim 1, wherein an artificial pixel is provided for each column of the matrix of photo-sensitive pixels, and wherein the photo-sensitive pixels and artificial pixels that are associated with the same column of the matrix have their outputs coupled to the same column line.

11. The image sensor according to claim 1, wherein, in the image read-out mode, the selecting circuitry and the read-out circuitry are configured for sequentially selecting a row of pixels of said matrix, said row including the dose sensing pixel in that row and for determining a pixel voltage for each of the selected pixels;
   wherein said determining of the pixel voltage for each of the selected pixels preferably comprises:
      resetting the photo-sensitive pixels in a row of interest;
      allowing the reset pixels to capture incoming photons during an integration time;
      after expiry of the integration time, reading out voltages associated with the pixels in the row of interest as first voltages;
      resetting the pixels in the row of interest and directly thereafter reading out voltages associated with these pixels as a second voltage; and
      determining pixel voltages for the pixels in the row of interest by subtracting the first voltages from the second voltages.

12. The image sensor according to claim 1, wherein, in the dose sensing mode, the selecting circuitry is configured for simultaneously selecting dose sensing pixels that are arranged in different rows and wherein the read-out circuitry is configured for determining a pixel voltage for each of the selected dose sensing pixels;
   wherein said determining of the pixel voltage for each of the selected dose sensing pixels preferably comprises:
      resetting the dose sensing pixels;
      allowing the dose sensing pixels to capture incoming photons;
      selecting the dose sensing pixels;
      reading out voltages associated with the selected dose sensing pixels as a first voltage;
      de-selecting the dose sensing pixels and selecting artificial pixels that are associated with the dose sensing pixels;
      reading out voltages associated with the selected artificial pixels as a second voltage; and
      determining the pixel voltages for the dose sensing pixels by subtracting the first voltages from the second voltages.

13. The image sensor according to claim 1, wherein at least the matrix of photosensitive pixels is covered with a scintillator layer for converting incoming X-ray photons into visible light photons.

14. An X-ray system, comprising:
   an X-ray source for emitting X-ray radiation; and
   an X-ray detector for detecting the emitted X-ray radiation, the X-ray detector including an image sensor comprising a plurality of photo-sensitive pixels arranged in a matrix of rows and columns, said plurality of photo-sensitive pixels having one or more dose sensing pixels, wherein the image sensor is operable in:
      a dose sensing mode, in which a dose of incoming photons is sensed using the one or more dose sensing pixels, and
      an image read-out mode, in which image information is determined using the matrix of pixels based on a received dose of incoming photons;
   one or more artificial pixels for providing a reference voltage in dependence of an input voltage;
   a pixel controller comprising selecting circuitry for selecting one or more rows of pixels in the matrix; and
   read-out circuitry configured for, in the dose sensing mode, reading out respective voltages of selected one or more dose sensing pixels and for determining a respective pixel voltage for each of the selected dose sensing pixels in dependence of the reference voltage and the voltage that was read out for that dose sensing pixel;
   wherein the image sensor further comprises one or more shielded photo-sensitive pixels that are shielded for incoming photons and which are each configured for outputting a further reference voltage, wherein the input voltage of the one or more artificial pixels is set in dependence on the outputted further reference voltage.

15. The X-ray system of claim 14, further comprising an optical camera.

\* \* \* \* \*